United States Patent [19]

Gur et al.

[11] 4,203,037
[45] May 13, 1980

[54] COLLIMATED RADIATION APPARATUS

[75] Inventors: David Gur; Donald Saskin; Ernest J. Sternglass, all of Pittsburgh, Pa.

[73] Assignee: University of Pittsburgh, Pittsburgh, Pa.

[21] Appl. No.: 957,016

[22] Filed: Nov. 6, 1978

Related U.S. Application Data

[63] Continuation of Ser. No. 820,423, Aug. 1, 1977, abandoned.

[51] Int. Cl.² ............................................. G03B 41/16
[52] U.S. Cl. ............................ 250/505; 250/416 TV; 250/490
[58] Field of Search ............... 250/505, 511, 512, 513, 250/439 R, 320, 321, 322, 323, 490, 416 TV

[56] References Cited

U.S. PATENT DOCUMENTS

| | | | |
|---|---|---|---|
| 3,668,402 | 6/1972 | Palermo | 250/510 |
| 3,822,362 | 7/1974 | Weckler | 178/7.1 |
| 3,991,316 | 11/1976 | Schmidt | 250/439 R |
| 4,096,391 | 6/1978 | Barnes | 250/505 |
| 4,097,748 | 6/1978 | Monvorsen | 250/505 |

OTHER PUBLICATIONS

"Investigation of Moving Slit Radiography," Sorenson Radiology, 9/76, pp. 705–711.

Primary Examiner—Craig E. Church
Attorney, Agent, or Firm—Arnold B. Silverman

[57] ABSTRACT

Apparatus for exposing an object to x-ray radiation including adjustable object supporting and compressing means and first collimator means having an opening and being disposed between the x-ray generator and the object supporting means. Second collimator means having an opening and being disposed between the object supporting means and x-ray detecting means. Means are provided for moving the first and second collimator means in such fashion as to maintain alignment between the openings therein and the x-ray generator, in order to sequentially expose portions of the object of x-ray passing through the first collimator means and permit such x-ray to pass through the opening in a second collimator means and impinge upon the x-ray detecting means. The object supporting and compressing means is preferably structurally independent of the collimator means.

The x-ray detecting means preferably takes the form of a highly sensitive detector such as a film-screen cassette or a self-scanning array of photodiodes optically coupled to scintillator means.

22 Claims, 12 Drawing Figures

COLLIMATED RADIATION APPARATUS

This is a continuation, of application Ser. No. 820,423, filed Aug. 1, 1977 now abandoned.

BACKGROUND OF THE INVENTION

1. Field of the Invention

This invention relates to apparatus for exposing an object to collimated x-ray radiation and providing further collimation so as to permit progressive exposure of the object to a limited quantity of x-ray radiation so as to provide improved x-ray image quality and/or a reduction in radiation exposure.

2. Description of the Prior Art

In the radiographic examination of various types of objects, including medical examination of parts of the human body, by the film-screen technique, the x-ray image quality tends to be reduced by the presence of scattered x-rays in the image. This problem is of particular concern in connection with the examination of certain anatomical structures, such as the female breast, for example, because the object contrast is normally very low, and any further reduction of this low contrast, because of scattered radiation, would result in the decreased ability to diagnose tumors, such as breast cancers, early in a stage when successful therapy is most likely to be available.

There is the further problem in connection with human examinations that it is undesirable to expose living human beings to any quantities of radiation beyond those reasonably necessary for diagnostic procedures. Even where such uses are desirable, as in attempts to detect the presence of female breast tumors, the frequency with which such examinations may be performed is somewhat limited as a result of a need to use an x-ray exposure sufficiently high so as to achieve an adequate quality of image. Efforts to reduce the exposure employed in such tests tend to move away from the desirable objective of increased contrast sensitivity in the resultant image.

It has previously been suggested to use various forms of collimators in connection with x-ray apparatus in order to better define the region which will be exposed to x-ray radiation. See, for example, U.S. Pat. Nos. 3,767,931; 3,829,701; 3,934,151; 3,947,689 and 3,973,177. These disclosures, however, do not provide synchronous movement of the pair of collimators which serve to severely restrict both the amount of x-ray impinging upon the object and the x-ray emerging from the object which is permitted to impinge upon the x-ray detector, such as the x-ray film or electronic sensors.

It has previously been suggested to employ a single mechanically moved slit collimator interposed between x-ray tube and patient with a phosphorus screen and associated camera lens, TV camera and cathode-ray tube display to provide for an image which may be recorded by means of a regular film camera. See Volume 78, Society of Photo-Optical Instrumentation Engineers, pages 108-112 ("Isocon Imaging for X-Ray Diagnostics") and Volume 70, Society of Photo-Optical Instrumentation Engineers, pages 384-392 ("An Evaluation of Low Light Level Television for Breast Cancer Detection"). In both of these systems, there is lacking any second slit collimator interposed between the test object and the x-ray detector means.

It has previously been known to employ an overlying collimator in combination with a member having scatter eliminating slots beneath a patient. See "Reduction of Scatter in Diagnostic Radiology by Means of a Scanning Multiple Slit Assembly" by Barnes, Cleare and Brezovich, pages 691-694, September 1976, *Radiology*. It has also been known to provide a pair of moving slotted collimators for minimizing the effects of scattered radiation. See "Investigations of Moving-Slit Radiography" by Sorenson and Nelson, pages 705-711, September 1976, *Radiology* and "A Method to Absorb Scattered Radiation without Attenuation of the Primary Beam" by Moore, Korbuly and Amplatz, pages 713-717, September 1976, *Radiology*.

None of these disclosures suggests the use of a pair of slit collimators in combination with independent object supporting and compressing means for compressing the object to a more uniform thickness to minimize the amount of thickness through which the x-ray must travel nor the beneficial combination of stationary supporting and compressing means used in combination with a pair of slit moving collimators. There is also lacking any disclosure of the beneficial combination of these elements with highly sensitive x-ray detector means, such as self-scanning arrays of photodiodes optically coupled to scintillator means or film-screen cassettes.

There remains, therefore, a substantial need for a means for improving the contrast sensitivity of x-ray techniques while minimizing the quantity of x-ray to which the object is exposed. This need is particularly significant in connection with radiography of patients, as in mammography.

SUMMARY OF THE INVENTION

The present invention has solved the above-described problems by providing an x-ray generator, a mechanically independent object supporting means, x-ray detecting means and first collimator means having an opening therein and being disposed intermediate the x-ray generator and the object supporting means and second collimator means having an opening therein and being disposed intermediate the object supporting means and the x-ray detecting means. Means are provided for synchronously moving the first and second collimator means so as to maintain the openings aligned with the x-ray focal point. As a result, the first collimator means limits the amount of the cone-shaped x-ray beam which will be imposed upon the specimen by converting the same to a narrow, fan-shaped beam. The second collimator permits passage of substantially only that portion of the x-ray that contains primary x-rays and forward scattered x-rays so as to preclude the major portion of scattered x-rays from reaching the x-ray detector. The object supporting and compressing means are preferably adjustable plates which permit independent compression of the object, such as a human female breast, to present a more uniform thickness to the x-ray and to minimize the amount of thickness of the object through which the x-ray must travel.

In addition, the present invention contemplates the use of extrasensitive x-ray detectors, such as film-screen cassettes and arrays of photodiodes optically coupled to scintillator means.

All of this and the additional features to be described hereinafter result in improved quality of image which permits early detection of smaller, and, therefore, earlier, cancerous tumors in breasts as well as other features which are not normally visible while permitting the use of reduced x-ray exposure.

It is an object of the present invention to provide a collimated x-ray apparatus which is adapted to minimize the effects of scattered radiation on the resultant x-ray image, thereby providing higher contrast pictures of superior clinical usefulness.

It is another object of this invention to provide an improved mammography system compatible with existing systems and of compact, lightweight construction so as to allow ready positioning in different orientations.

It is another object of this invention to provide apparatus adapted to image smaller density differences.

It is a further object of the present invention to provide such an apparatus which is adapted to include high sensitivity x-ray detector means.

It is another object of the present invention to provide such apparatus wherein high contrast sensitivity imaging is accomplished without the need for increased radiation exposure or exposure time.

It is another object of the present invention to provide adjustable means for supporting and compressing an object to provide greater uniformity of thickness.

It is another object of this invention to provide such a system which is compatible with existing x-ray equipment and is of relatively small size and weight.

It is another object of this invention to provide such apparatus which employs synchronized movement of a pair of collimator openings which sequentially permit brief exposure of portions of the object to x-rays so as to minimize the effect of object motion.

It is yet another object of this invention to provide such apparatus which is particularly suited to the examination of the female breast in determination of the existence of potential malignant tumors at a minimum of radiation exposure.

These and other objects of the invention will be more fully understood from the following description of the invention on reference to the illustrations appended hereto.

DESCRIPTION OF THE PREFERRED EMBODIMENTS

As used herein, the expression "object" or "test object" will refer to various types of objects to be exposed to x-ray radiation including medical tests wherein portions of the human or animal body are exposed to x-ray in such fashion as to produce data which is related to the structure exposed. While for purposes of clarity of description, specific reference will be made herein to use in medical environments and, more specifically, in x-ray diagnostic procedures on female breasts, it will be appreciated that other forms of medical tests objects, specimens, as well as other test specimens (such as products to be nondestructively tested) may be tested in connection with the x-ray apparatus of the present invention, and, in addition to the preferred medical uses, such other uses are expressly contemplated.

As used herein, the term "x-ray detecting means" shall include various forms of means for receiving x-rays and converting the same into visible images, stored electron charges or other functions of the intensity of x-ray received which permits individuals to appraise the results of the x-ray exposure of the particular test object. Specifically included within the definition are light-sensitive or x-ray sensitive film, an intensifying screen employed in combination with an x-ray film disposed inside a vacuum cassette, arrays of semiconductor diodes, such as a self-scanning array of photodiodes optically coupled to scintillator means (such as phosphor screens, image intensifier tubes and solid-state intensifier panels, for example), high resolution television cameras, means for recording the image in analog form or converting the same to digital form for computer processing analysis and display, as well as a simple photodetector of either solid state or vacuum tube type. More than one of these means may be provided in the same apparatus.

Figures 1, 1A:
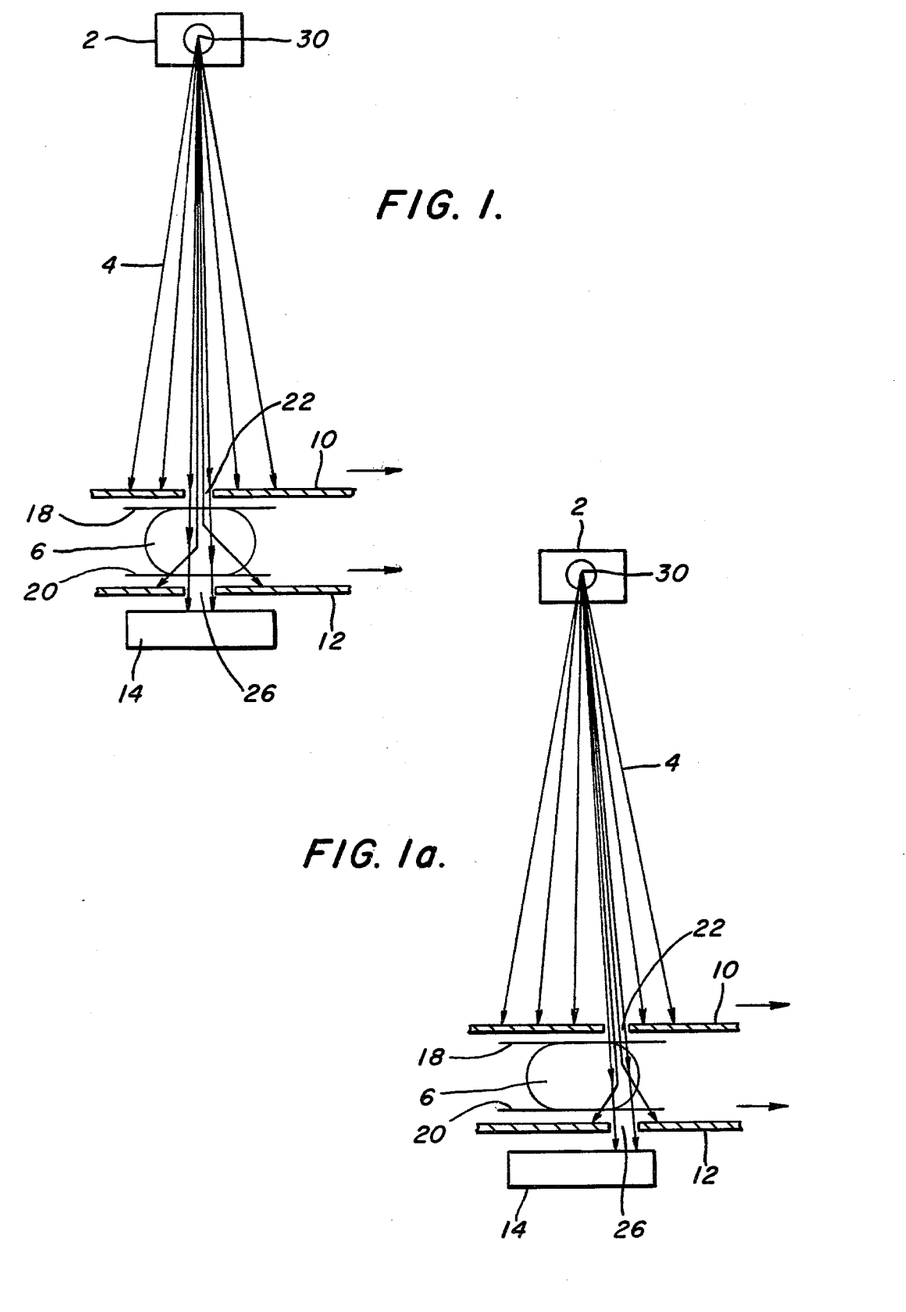
FIG. 1 is a schematic illustration of a form of x-ray apparatus of the present invention.
FIG. 1a is substantially similar to FIG. 1 except that the collimator means have been moved with respect to the object.

Referring now more specifically to FIG. 1, there is shown schematically a form of the present invention. As is there shown, an x-ray tube 2 emits a cone-shaped x-ray beam 4 which has a portion passing through first collimator means 10 and second collimator means 12 and into x-ray detector means 14. It is noted that the first collimator means 10 has an opening 22 which permits only a fan-shaped portion of x-ray beam 4 to pass therethrough and enter object 6. The remaining portion of the x-ray beam 4 is shielded from the object by first collimator means 10. It is further noted that second collimator means 12 has an opening 26 which limits the portion of the x-ray beam which passes through second collimator means 12 into x-ray detector 14. Opening 26 permits only primary x-rays and forward scattered x-rays to pass onto x-ray detector 14. It is also noted that openings 22 and 26 are generally aligned with each other and with x-ray focal point 30. In the form shown in FIG. 1, the first and second collimator means 10, 12 are moving generally to the right side of the figure while the object 6 is retained in relatively stationary position with respect to x-ray generator 2 by means of object supporting means 18, 20.

Referring now to FIG. 1a, it is seen that the collimator means 10, 12 have moved to the right, and the pair of aligned openings 22, 26 now permit x-ray passage through a different portion of the object 6. It is also noted that in order to preserve the desired alignment between openings 22, 26 and focal point 30, that the opening 26 has moved farther to the right than has the opening 22. The means for effecting this movement will be discussed below.

In a preferred form, while second collimator means 12 will move at a faster velocity than first collimator means 10, each collimator means 10, 12 will move in its respective path at a substantially constant velocity.

Figure 2:
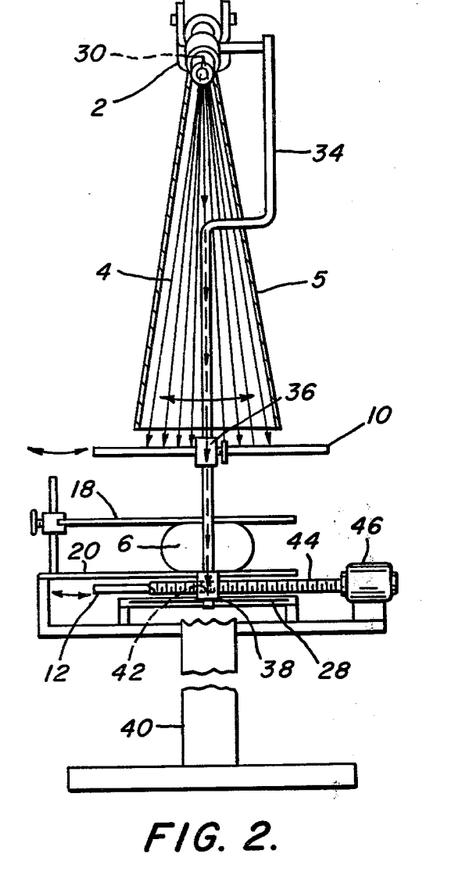
FIG. 2 is a more detailed schematic of a form of apparatus suitable for use with the present invention.
Figure 3:
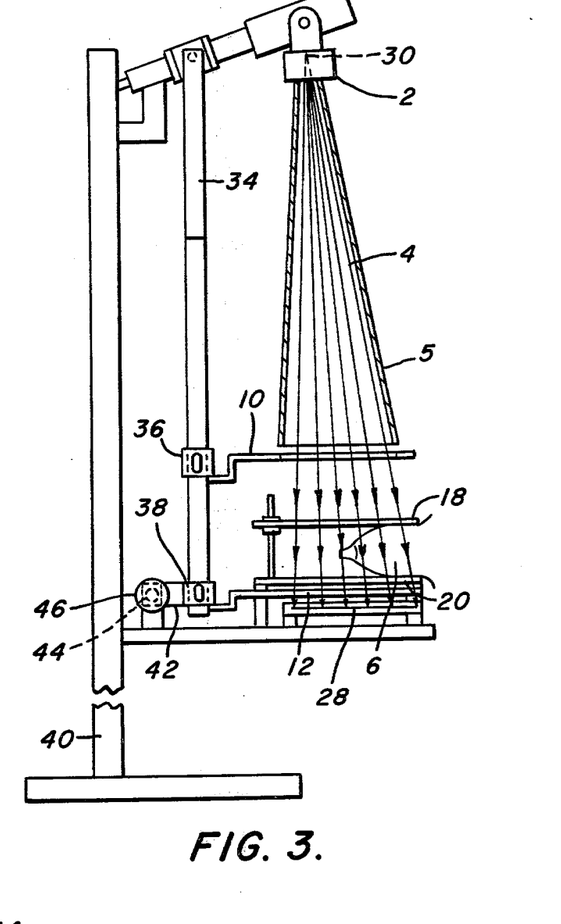
FIG. 3 is a side elevational view of the apparatus shown in FIG. 2.
Figure 4:
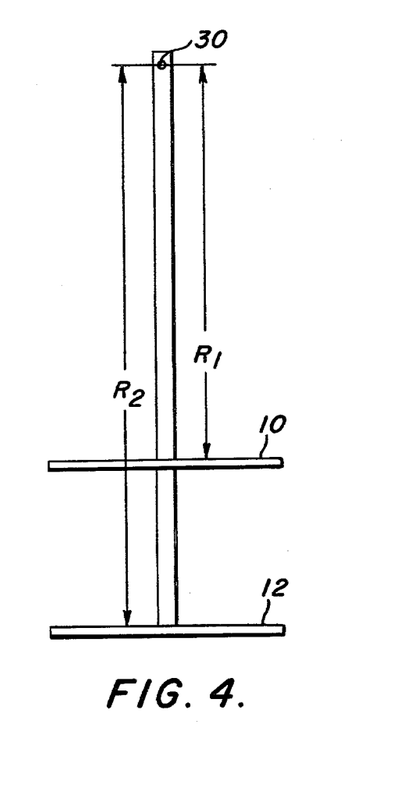
FIG. 4 is an illustration of a form of collimator means and mounting therefor.

Referring now to FIGS. 2 through 4, a means for effecting relative, synchronized movement between first collimator means 10 and second collimator means 12 will be considered in greater detail. Radiation beam limiting cone 5 confines the conical x-ray beam 4. The radiation passing through second collimator means 12 impinges on film cassette 28. Pivot arm 34 is preferably substantially rigid and contains an upper portion which is pivotally mounted with respect to x-ray focal point 30 and has a first collimator means 10 and second collimator means 12 fixedly secured thereto in generally parallel relationship with respect to each other. As is shown in FIG. 4, first collimator means 10 is at a distance $R_1$ from the x-ray focal point 30 about which pivot arm 34 pivots, and second collimator means 12 is a greater distance $R_2$ from the x-ray focal point 30. As a result, rotation of the pivot arm 34 about x-ray focal point 30 will result in second collimator means 12 moving at a greater velocity than first collimator means 10. This, in turn, permits the opening 26 in second collimator means 12 to move farther than the opening 22 in first collimator means 10 during any given time interval and permits creation of the relative, aligned positions shown in FIGS. 1 and 1a.

As is shown in FIG. 3, first clamp member 36 secures first collimator means 10 to pivot arm 34. Second clamp member 38 secures second collimator means 12 to pivot arm 34 and has a portion 42 threadedly engaged with drive screw 44 in such fashion that rotation of drive screw 44 by motor 46 will result in relative longitudinal displacement of portion 42 of clamp 38 along drive screw 44 with the result that second collimator means 12 and pivot arm 34 will be provided with responsive movement, and first collimator means 10 will also be moved. In the preferred form, the motor 46 will operate at a substantially constant speed to move said first collimator means 10 at a first substantially constant velocity and said second collimator means 12 at a second substantially constant velocity. In the present invention, it is contemplated that the first and second collimator means 10, 12 will be subjected to relative reciprocating movement with respect to object 6 in such fashion that portions of the object 6 will progressively be exposed to radiation.

Figure 5:
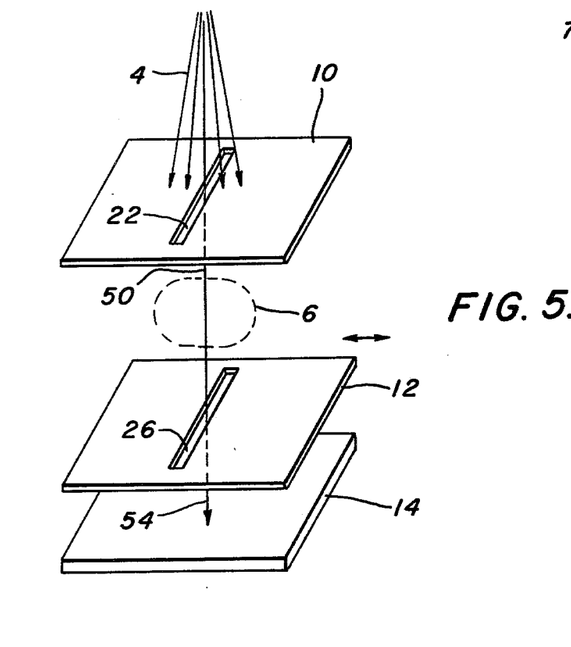
FIG. 5 is a schematic illustration of a form of collimator means of the present invention.

As is shown generally in FIG. 5, the conical x-ray beam impinges upon the upper surface of first collimator means 10 with slit 22 serving to permit passage therethrough of solely a fan-shaped beam 50 which passes through object 6. As a result of slit 26 in second collimator means 12 being aligned with the x-ray focal point 30 (not shown in this view) and slit 22, as to the radiation passing through object 6, solely the primary radiation and forward scattered x-rays are permitted to pass through slits 26 and provide beam 54 which impinges upon x-ray detector 14. As the collimators 10, 12 continue their progressive synchronized movement with respect to object 6, sequentially each portion of the object desired to be exposed to the x-ray will be exposed in this fashion in order to generate a complete picture of the object or portions thereof. It is contemplated that movement from one end of the object to the other so as to provide a complete scan may be accomplished in a matter of about two to four seconds. This results in any movement of the object tending to be arrested and further improvement in the quality of the image. For a single x-ray, it will be appreciated that it will be necessary to traverse the object only in a single direction. However, the advantageous use of a reversing motor permits a second x-ray of the same object to be taken in the reverse direction or serves to minimize the amount of setup required for the next object. It will be appreciated, however, that a single traverse is all that is required to obtain a complete picture.

Figure 6:
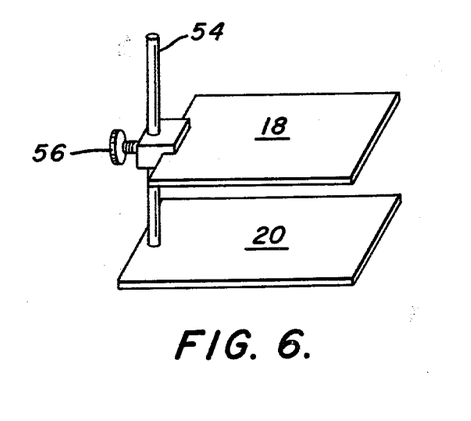
FIG. 6 is a schematic illustration of a form of object supporting means of the present invention.

Referring now to FIG. 6, the object supporting means will now be considered in greater detail. In order to minimize the amount of thickness through whih the x-ray must pass and also to provide a more uniform thickness, as in the case of a female breast, it is desirable to adjust the spacing between the plate-like members 18, 20 which, in the form shown, serve to provide the mechanical support of the object, independent of the moving slit collimators, i.e. the object is supported and compressed while being out of direct contact with the moving slit collimators. This independence contributes to alignment of the collimator slits through which the x-ray passes, independent of the thickness of the breast. In the form illustrated, a post member 54 is supported by plate-like member 20 and is adjustably positioned with respect to plate-like member 18 by means of clamp 56. Opening and closing of clamp 56 permits relative separating or closing movement between plate-like members 18 and 20. It will also be appreciated that after fixing the position of plate-like members 18, 20 with respect to the object, the object and the plate-like members 18, 20 remain in fixed position with respect to the moving first and second collimator means 10, 12, in the form shown.

As has been mentioned above, one of the objectives of the present invention is to obtain an image of higher diagnostic quality while subjecting the object to either no increase in x-ray exposure or, in fact, achieving a reduction therein. In a preferred embodiment of the invention, not only will the above-described collimator and object supporting system contribute meaningfully to the attainment of this objective, but also highly sensitive x-ray detection means are employed in combination to provide the optimum desired system.

Figure 7:
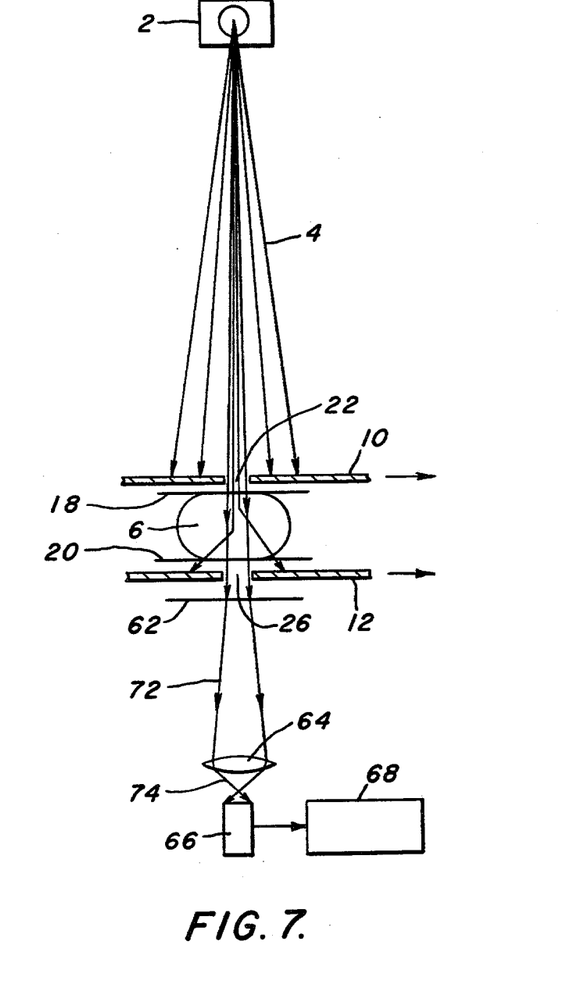
FIG. 7 discloses a schematic illustration of a modified form of the present invention employing a different form of x-ray detecting means.

Referring now to FIG. 7, one form of such an improved x-ray detector means will now be considered. In the form of the system illustrated in FIG. 7, the x-ray beam emerging through slit 26 in second collimator means 12 impinges upon an x-ray sensitive scintillator 62, such as an x-ray luminescent screen, which serves to convert the impinging x-ray beam into a light beam 72 which has an intensity and distribution corresponding to the x-ray beam received. The light beam 72 impinges upon optical coupling means which, in the form shown, is lens 64 which provides converging light beam 74, which impinges upon the light sensitive detector which, in the form shown, is preferably a linear self-scanning array of photodiodes. The sensitivity of the phothodiodes coupled with the ability to produce a highly refined group of signals as a result of the relatively small size of the photodiodes contributes meaningfully to the improved contrast sensitivity. A discussion of self-scanning photodiode arrays is found in the United States patent application entitled "Radiography Apparatus", Serial No. 820,424, filed of even date herewith by Ernest Sternglass and Donald Sashin. Self-scanning photodiode arrays have previously been known to be used in a number of environments. See, for example, "Self-Scanning Photodiode Arrays for Spectroscopy" by E. H. Snow in the April 1976 issue of *Research/Development*. See also U.S. Pat. Nos. 3,717,770; 3,801,820; 3,822,362; 3,947,630; 3,955,082 and 3,993,888. The electrical output of photodiode array 66 is a group of electrical signals, which are a function of light beam 74, is introduced into signal receiving means 68. These electrical signals may be employed in providing a direct image as by use of a TV monitor or, alternatively, or in addition, may be stored in analog or digital fashion, recorded on a chart, computer altered or treated in any desired fashion. The important result is that a high quality reading has been obtained so as to provide improved ability to observe the interior structure of the object with a high degree of contrast sensitivity while minimizing the quantity of x-ray exposure to which the object has been exposed. While, for purposes of simplicity of illustration, the optical coupling means 64 has been shown to be a lens, it will be appreciated that in lieu thereof, reflecting mirrors, fiber optic means, image intensifiers or other suitable means of causing the light beam 72 to be effectively transmitted to the photodiode array 66 may be employed.

As an alternative to the photodiode array described in connection with FIG. 7, an electronic television camera may be provided at 66 and be optically coupled to an intensifying phosphor screen positioned at 62. This camera may be of any suitable type, including solid-state cameras of the self-scanning type. It may also be of the analog or digital type for image processing, storage and display.

Figure 8:
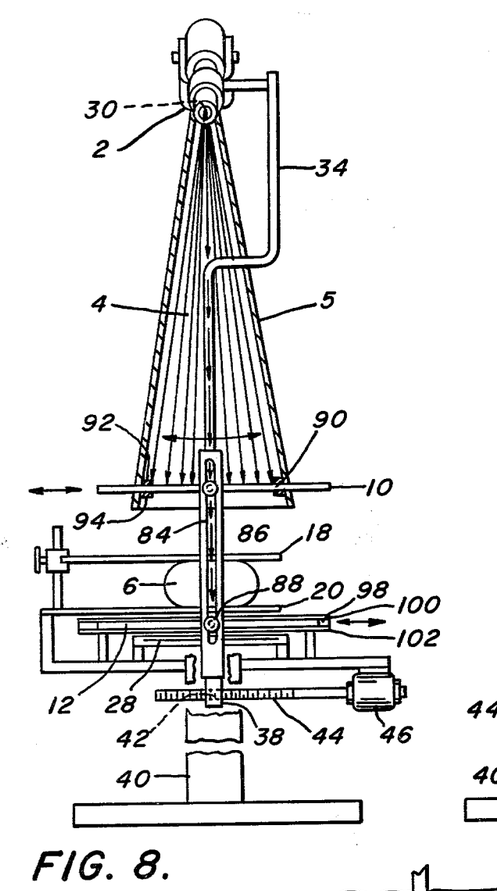
FIG. 8 is a schematic front elevation of another embodiment of the invention.
Figure 9:
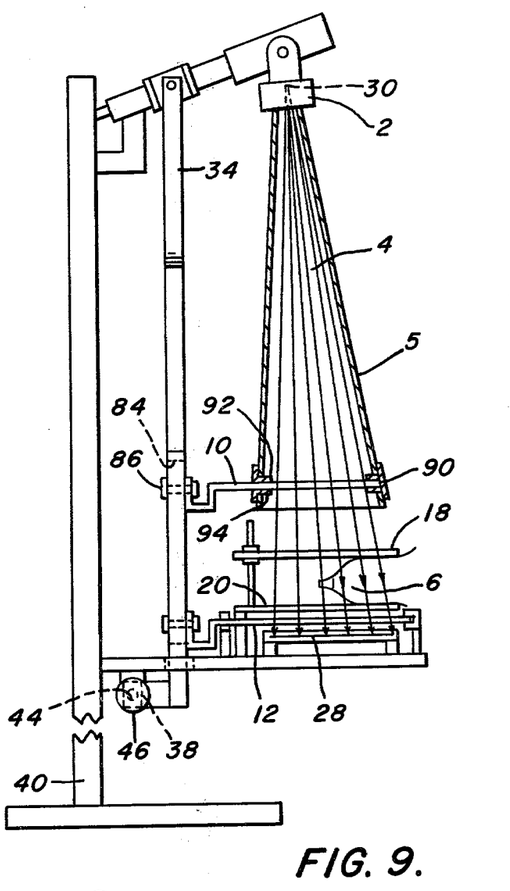
FIG. 9 is a side elevational view of the apparatus shown in FIG. 8.
Figure 10:
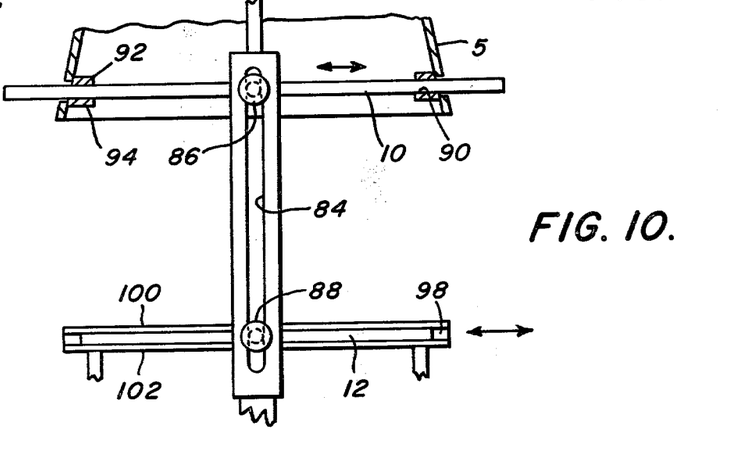
FIG. 10 is a detail of a portion of the embodiment shown in FIGS. 8 and 9 illustrating the collimator linkage.

Referring now to FIGS. 8 through 10, a modified means for effecting movement of the collimator plates 10, 12 will now be considered. In the embodiment of FIGS. 2 and 3, the pivot arm 34 rotates about x-ray focal point 30 and rigidly attached collimator means 10, 12 move in an arc-like path. In the embodiment of FIGS. 8 through 10, the pivot arm 34 moves in the same path pivoting about focal point 30, but, as a result of a different connection between the pivot arm 34 and collimator means 10, 12 and the use of guideways, the collimator 10, 12 are subjected to responsive reciprocating linear movement as shown by the arrows.

In this embodiment, the lower end of pivot arm 34 is provided with an elongated slot 84. Retainer members 86, 88 rotatably secure, respectively, collimator means 10, 12 to the pivot arm 34. In the form shown, the retainer members 86, 88 have enlarged heads at the ends of greater diameter than the width of slot 84 and a connecting cylindrical portion of smaller diameter than the width of slot 84. This permits both relative sliding movement of retainer members 86, 88 within slot 84 and relative rotational movement between the retainer members 86, 88 and slot 84.

In order to establish the controlled responsive linear movement of collimator means 10, 12 responsive to rotation of pivot arm 34, guideway means are provided. In the form shown, the upper guideway means which define the path of movement of collimator means 10 are provided by a downward extension of the radiation beam limiting cone 5. The collimator means 10 has its outer free end slidingly received within channel 90 and an inner portion slidably received between flanges 92, 94. The channel 90 and guideway defining members 92, 94 are of sufficient length that linear movement of collimator means 10 will not result in either longitudinal end thereof becoming disengaged from the upper guideway means. Similarly, lower guideway means are provided by channel member 98 and guideway defining members 100, 102.

Figure 11:
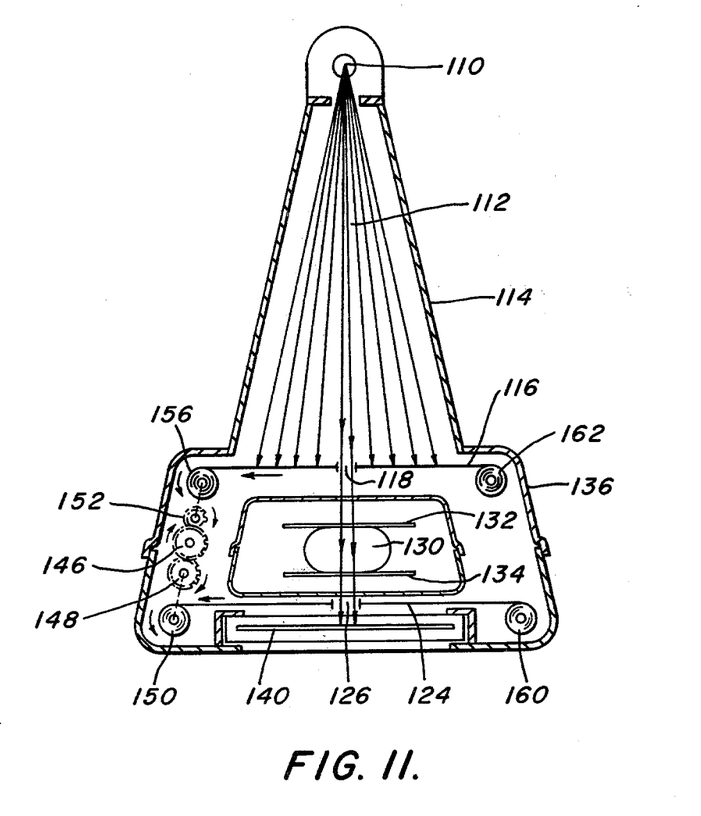
FIG. 11 is a schematic of another embodiment of the invention.

Referring now to FIG. 11, another embodiment will be considered. In this embodiment, which may be employed advantageously in mammography, a different form of collimator means will be considered. In this embodiment, a pair of belts made of suitable x-ray opaque material, such as lead-impregnated rubber, for example, are employed. An x-ray source 110 provides an x-ray beam 112 within a radiation beam limiting cone 114 which is secured to multi-piece housing 136. Upper collimator belt 116 has slit 118, and lower collimator belt 124 has slit 126. The lower belt 124 is adapted to move more rapidly than the upper belt 116 in order to maintain the aligned position between the x-ray focal point and slits 118 and 126. The object 130 is supported and compressed by plate-like means 132, 134. The x-ray beam 112 has a fan-shaped portion pass through slit 118, then through the object 130 and through slit 126 to x-ray detector means 140.

Upper belt 116 has one end secured to rotatable idler spool 162 and the other end to driven spool 156. Lower belt 124 has an end secured to idler spool 160, and the other end secured to driven spool 150. A motor (not shown) drives gear 146. Gear 146 meshes with gear 152 which, in turn, meshes with driven spool 156. Gear 146 also meshes with gear 148 which, in turn, meshes with driven spool 150. The gear ratios are so selected as to provide the desired faster movement of slit 126 with respect to slit 118. If desired, separate motors may be employed to drive spools 150, 156 and electrical means employed to coordinate relative speed. Also, a chain or belt drive could be substituted for the gear drive if desired. Any suitable manual or automatic means may be employed to rewind the belts 116, 124 before the next use of the equipment. For example, the drive equipment shown at the left of FIG. 11 may be duplicated at the right for automatic rewinding.

The embodiment of FIG. 11 offers the advantages of compactness, a fully enclosed mechanism with no projecting plates and the ability to separate the upper and lower housing portions for easier patient placement.

The collimator means should be made from an x-ray opaque material, such as lead, tungsten, tantalum or lead-impregnated rubber (for the belt embodiment). The object support means should be made of an x-ray transparent material, such as an ester based material of low atomic number. Materials sold under the trade designations Mylar and Lexan are suitable.

The present invention also facilitates the advantageous use of relatively high energy, filtered x-ray beams on the order of about 35-45 kVp as compared with the more conventional range of about 25-35 kVp. A suitable filter for removing low energy x-rays would be aluminum in a thickness of about 1.0 to 2.5 mm.

The apparatus of the present invention also provides an additional means for improving contrast detectability. The "air gap", which is the distance between the exit side of the object and the x-ra detector means, may be increased to reduce the intensity of the scattered radiation which impinges on the detector means. An enlarged air gap is shown in FIG. 7 as compared with that shown in FIG. 3, for example.

It will therefore be appreciated that the present invention provides improved means for obtaining high contrast sensitivity imaging while subjecting the object to no increased x-ray dosages and preferably reduced dosages thereof. This is accomplished preferably by a combination of a uniquely designed double-slit collimator construction which effects synchronous movement across the object so as to sequentially expose portions thereof to the x-ray while shielding against undesired penetration of x-rays, either into the object or out of the object into the x-ray detector means. It also provides for increased sensitivity x-ray detector means so as to improve the imaging contrast sensitivity. All of this is accomplished in simple, economical fashion while permitting the continued use of conventional equipment, such as existing x-ray generators and tubes. The compatibility with respect to the same facilitates rapid and economic adoption of the system of the present invention.

By using very sensitive x-ray detecting means, such as a self-scanning array of photodiodes or an x-ray film-screen combination, a number of advantages are obtained. This approach permits reduction of the heat load on the x-ray tube when only a narrow fan-shaped beam of the total x-ray beam is being used, thereby permitting use of a finer focal spot which, in turn, gives a more detailed image. Increased scan speeds which reduce the likelihood of blurring due to object movement are facilitated. In addition, the increase in scan speed further reduces object radiation exposure time. For example, if the total scan time is about two seconds and the collimator opening is 1/20 of the field width, the object will be exposed for only 1/10 seconds. Any reduction in total scan time would proportionately reduce exposure time.

The system is particularly suited, but not limited to, use with objects in the form of a female breast for cancer detection techniques. The object supporting and compressing means provides for an object of essentially uniform thickness and minimum depth, and the scanning procedure involving the slit collimators and having sensitive x-ray detectors permits unusually high contrast sensitivity while using low levels of radiation. This permits not only improved results as to a particular screening, but also opens the possibility of more frequent testing in order to obtain diagnosis of breast cancer at an early stage when successful treatment is most likely to be possible.

It will be appreciated that while certain preferred embodiments and the best mode presently known to the inventors for practicing the invention have been disclosed herein, modifications may be made from this specific disclosure while preserving the benefits of the present invention and remaining within the scope thereof. For example, while the use of a drive screw to establish synchronous movement of the collimator means has been employed and such screw has been operatively associated with the second collimator means 12, the drive screw might be associated with other portions of the pivot arm or collimator means. Also, alternate means of establishing the desired synchronous movement of the two plate-like collimators will be readily apparent to others. For example, each collimator 10, 12 could be mounted within guideways and independently powered by separate motors for movement relative to the object with electrical means being employed to coordinate the relative motor speeds so as to preserve collimator slit alignment with the x-ray focal point.

While the collimator means 10, 12, 116, 124 have been shown as each having a single opening or slit, it is contemplated that for certain uses it may be advantageous to provide more than one opening in each collimator. For example, if two openings were so positioned in each collimator as to be simultaneously aligned with the x-ray focal point 30, the amount of collimator movement required to expose an object to the x-ray beam would be cut in half, and the energy employed to generate the x-ray beam would be used more efficiently. Similarly, additional openings beyond two per collimator may be provided.

Whereas, particular embodiments of the invention have been described above for purposes of illustration, it will be evident to those skilled in the art that numerous variations of the details may be made without departing from the invention as defined in the appended claims.

We claim:

1. Apparatus for exposing an object to x-ray radiation comprising,
   an x-ray generator,
   adjustable object supporting and compressing means disposed generally in the path of x-ray emission from said generator for supporting and compressing said object,
   first collimator means having an opening therethrough and being interposed between said x-ray generator and said object supporting and compressing means,
   x-ray detecting means disposed on the opposite side of said object supporting and compressing means from said x-ray generator,
   second collimator means having an opening therethrough and being disposed between said object supporting and compressing means and said x-ray detecting means,
   said x-ray detecting means including
      (a) scintillator means for receipt of x-rays passing through said second collimator means opening and emitting light responsive thereto,
      (b) an array of self-scanning photodiodes for receipt of said light and converting the same into electrical output signals, and
      (c) optical coupling means interposed between said scintillator means and said array of self-scanning photodiodes,
   said x-ray detecting means being spaced from said object supporting and compressing means,
   signal receiving means operatively associated with said self-scanning photodiode array to receive said electrical signals therefrom, whereby said electrical signals corresponding to said x-ray passage through said second collimator means opening may be stored, processed or displayed,
   means for effecting movement of said first and second collimator means relative to and independent of said object supporting and compressing means, and
   said means for effecting movement of said first and second collimator means effecting synchronized movement thereof so as to maintain said collimator openings in aligned relationship with respect to said x-ray generator, whereby an object supported and compressed by said object supporting and compressing means will have portions thereof sequentially exposed to x-rays which pass through said opening in said first collimator means and after passing through said object will pass through said aligned opening in said second collimator means and will then impinge upon said x-ray detecting means.

2. The x-ray apparatus of claim 1 including said object supporting and compressing means including a pair of spaced, generally parallel plate-like members, and adjusting means for altering the relative spacing between said plate-like members, whereby said plate-like members may be employed to compress said object to establish a more uniform object thickness, independently of the positions of said first and second collimator means.

3. The x-ray apparatus of claim 2 including said object supporting and compressing means being oriented generally perpendicularly with respect to the path of x-ray emission from said x-ray generator, and apart from relative separating and closing movement between said plate-like members, said object supporting and compressing means being generally fixedly secured with respect to said x-ray generator, whereby movement of said first and second collimator means with respect to said object supporting and compressing means will result in sequential exposure of different portions of said object to said x-ray through said first collimator means opening.

4. The x-ray apparatus of claim 2 including said object supporting and compressing means plate-like members adapted to open sufficiently to permit introduction therebetween of an object which is a human female breast and adapted to close sufficiently to permit compression of said breast in order to establish a more uniform thickness and reduced depth of object for x-ray passage therethrough.

5. The x-ray apparatus of claim 1 including said first collimator means being a first belt member, and said second collimator means being a second belt member.

6. The x-ray apparatus of claim 5 including said means for effecting movement of said first and second collimator means including a first driven spool operatively associated with said first belt member, a second driven spool operatively associated with said second belt member, motor means and gear means operatively associated with said first and second driven spools.

7. The x-ray apparatus of claim 6 including said gear means having means to rotate said second driven spool at a faster rate than said first driven spool.

8. The x-ray apparatus of claim 1 wherein said optical coupling means includes lens means.

9. The x-ray apparatus of claim 1 wherein said first collimator means is a generally plate-like member, said second collimator means is a generally plate-like member, and said first and second collimator means are mounted generally parallel to each other.

10. The x-ray apparatus of claim 9 including said means for effecting movement of said first and second collimator means having means for establishing relative reciprocating movement of said first and second collimator means with respect to said object supporting and compressing means.

11. The x-ray apparatus of claim 10 including said means for effecting movement having means for moving said second collimator means at a faster rate than said first collimator means.

12. The x-ray apparatus of claim 11 wherein said means for effecting movement including a pivot arm to which said first and second collimator means are fixedly secured.

13. The x-ray apparatus of claim 12 including said pivot arm being rotatable about a pivot disposed generally at the x-ray focal spot.

14. The x-ray apparatus of claim 12 including said means for effecting movement including motor means and transmission means operatively associated therewith for effecting movement of said first collimator means, said second collimator means and said pivot arm as a unit.

15. The x-ray apparatus of claim 14 including said transmission means including a drive screw operatively associated with said second collimator means.

16. The x-ray apparatus of claim 11 including said means for effecting movement having means for moving said first and second collimator means in a generally arc-like path.

17. The x-ray apparatus of claim 11 including said means for effecting movement having means for moving said first and second collimator means in a linear path.

18. The x-ray apparatus of claim 17 including said means for effecting linear path movement having a pivot arm, linkage means connecting said pivot arm to said first and second collimator means and guideway means for defining linear paths of movement for said first and second collimator means.

19. The x-ray apparatus of claim 18 including said pivot arm having an elongated slot therein, first retainer means passing through said pivot arm slot connecting said first collimator means to said pivot arm while permitting relative rotational and sliding movement between said pivot arm and said first collimator means, and second retainer means passing through said pivot arm slot connecting said second collimator means to said pivot arm while permitting relative rotational and sliding movement between said pivot arm and said second collimator means.

20. The x-ray apparatus of claim 19 including said guideway means including upper guideway means defining a linear path for said first collimator means and lower guideway means defining a linear path for said second collimator means with said paths being substantially parallel.

21. The x-ray apparatus of claim 20 including an x-ray beam limiting cone depending from said x-ray generator, and said upper guideway means disposed within the lower extremity of said x-ray beam limiting cone.

22. The x-ray apparatus of claim 9 including said means for effecting movement of said said first and second collimator means having means for moving said first collimator means at a first substantially constant velocity and means for moving said second collimator means at a second substantially constant velocity.

* * * * *